(12) United States Patent
Paley et al.

(10) Patent No.: US 7,813,591 B2
(45) Date of Patent: Oct. 12, 2010

(54) VISUAL FEEDBACK OF 3D SCAN PARAMETERS

(75) Inventors: Eric B. Paley, Cambridge, MA (US);
Ilya A. Kriveshko, Littleton, MA (US);
Joseph Boeries, Medford, MA (US);
Steven V. Weeks, North Andover, MA (US); Edward K. Tekeian, Cambridge, MA (US); Janos Rohaly, Acton, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 1072 days.

(21) Appl. No.: 11/469,871

(22) Filed: Sep. 3, 2006

(65) Prior Publication Data
US 2007/0172112 A1    Jul. 26, 2007

Related U.S. Application Data (60) Provisional application No. 60/761,078, filed on Jan. 20, 2006.

(51) Int. Cl.
*G06K 9/36* (2006.01)
*G06K 9/00* (2006.01)

(52) U.S. Cl. .................. 382/285; 382/108; 382/154; 382/128; 345/418; 345/589; 345/629; 345/649

(58) Field of Classification Search .............. 382/100, 382/103, 106, 108–109, 128–132, 153–154, 382/285, 293–296; 345/418–424, 589, 629–634, 345/649–688
See application file for complete search history.

(56) References Cited

U.S. PATENT DOCUMENTS

| | | | |
|---|---|---|---|
| 4,270,901 A | | 6/1981 | Comparetto |
| 4,837,732 A | | 6/1989 | Brandestini et al. |
| 4,846,684 A | | 7/1989 | Oestreich |
| 5,372,502 A | * | 12/1994 | Massen et al. ............. 433/215 |
| 5,417,572 A | | 5/1995 | Kawai et al. |
| 5,644,386 A | * | 7/1997 | Jenkins et al. ............. 356/4.01 |
| 5,740,222 A | * | 4/1998 | Fujita et al. .................. 378/4 |
| 5,740,802 A | | 4/1998 | Nafis et al. |
| 5,771,310 A | * | 6/1998 | Vannah ........................ 382/154 |
| 5,999,840 A | * | 12/1999 | Grimson et al. ............ 600/424 |
| 6,044,232 A | * | 3/2000 | Pan ............................ 396/330 |
| 6,099,314 A | | 8/2000 | Kopelman et al. |
| 6,141,105 A | * | 10/2000 | Yahashi et al. ............. 356/623 |
| 6,201,541 B1 | | 3/2001 | Shalom et al. |
| 6,201,880 B1 | | 3/2001 | Elbaum et al. |
| 6,201,889 B1 | * | 3/2001 | Vannah ........................ 382/131 |

(Continued)

FOREIGN PATENT DOCUMENTS

DE    10 2005 016 245 A1    10/2006

(Continued)

OTHER PUBLICATIONS

European Search Report, 62701EP008, PCT/US2007/001547, May 11, 2010.

(Continued)

*Primary Examiner*—Manav Seth (57) ABSTRACT

The systems and methods disclosed herein provide visual feedback concerning one or more scanning parameters to a user during acquisition of a three dimensional scan.

17 Claims, 8 Drawing Sheets

U.S. PATENT DOCUMENTS

| | | | |
|---|---|---|---|
| 6,334,853 B1 | 1/2002 | Kopelman et al. | |
| 6,342,917 B1* | 1/2002 | Amenta | 348/207.1 |
| 6,364,660 B1 | 4/2002 | Durbin et al. | |
| 6,409,504 B1 | 6/2002 | Jones et al. | |
| 6,447,453 B1* | 9/2002 | Roundhill et al. | 600/443 |
| 6,512,838 B1* | 1/2003 | Rafii et al. | 382/106 |
| 6,516,213 B1* | 2/2003 | Nevo | 600/424 |
| 6,542,249 B1 | 4/2003 | Kofman et al. | |
| 6,545,637 B1* | 4/2003 | Krull et al. | 342/357.09 |
| 6,621,491 B1 | 9/2003 | Baumrind et al. | |
| 6,648,640 B2 | 11/2003 | Rubbert et al. | |
| 6,687,393 B1 | 2/2004 | Skinner, Jr. | |
| 6,701,006 B2 | 3/2004 | Moore et al. | |
| 6,738,063 B2* | 5/2004 | Shen et al. | 345/424 |
| 6,738,727 B2 | 5/2004 | Chang | |
| 6,754,370 B1 | 6/2004 | Hall-Holt et al. | |
| 6,775,404 B1* | 8/2004 | Pagoulatos et al. | 382/154 |
| 6,819,318 B1 | 11/2004 | Geng | |
| 6,834,119 B2 | 12/2004 | Chen | |
| 6,856,321 B2 | 2/2005 | Tsukizaki et al. | |
| 6,920,242 B1 | 7/2005 | Moore et al. | |
| 6,947,038 B1 | 9/2005 | Anh et al. | |
| 6,996,261 B2* | 2/2006 | deCharms | 382/131 |
| 7,010,150 B1 | 3/2006 | Pfeiffer et al. | |
| 7,020,325 B2 | 3/2006 | Park | |
| 7,061,485 B2 | 6/2006 | Tanguay, Jr. et al. | |
| 7,103,212 B2 | 9/2006 | Hager et al. | |
| 7,112,065 B2 | 9/2006 | Kopelman et al. | |
| 7,133,042 B2 | 11/2006 | Anh et al. | |
| 7,162,075 B2 | 1/2007 | Littlefield et al. | |
| 7,194,112 B2 | 3/2007 | Chen et al. | |
| 7,245,743 B2 | 7/2007 | Littlefield et al. | |
| 7,280,682 B2 | 10/2007 | Littlefield et al. | |
| 7,286,954 B2 | 10/2007 | Kopelman et al. | |
| 7,373,286 B2 | 5/2008 | Nikolskiy et al. | |
| 7,428,481 B2 | 9/2008 | Nikolskiy et al. | |
| 7,545,372 B2 | 6/2009 | Kopelman et al. | |
| 2002/0055800 A1 | 5/2002 | Nikolskiy et al. | |
| 2002/0102009 A1 | 8/2002 | Jones et al. | |
| 2002/0180760 A1 | 12/2002 | Rubbert et al. | |
| 2004/0029078 A1 | 2/2004 | Marshall | |
| 2004/0155975 A1 | 8/2004 | Hart et al. | |
| 2004/0179728 A1 | 9/2004 | Littlefield et al. | |
| 2004/0204787 A1 | 10/2004 | Kopelman et al. | |
| 2004/0220691 A1 | 11/2004 | Hofmeister et al. | |
| 2005/0007082 A1 | 1/2005 | Bretz et al. | |
| 2005/0070782 A1 | 3/2005 | Brodkin | |
| 2005/0153255 A1 | 7/2005 | Sporbert et al. | |
| 2005/0153257 A1 | 7/2005 | Durbin et al. | |
| 2005/0170309 A1 | 8/2005 | Raby et al. | |
| 2006/0003292 A1 | 1/2006 | Lauren et al. | |
| 2006/0093988 A1 | 5/2006 | Swaelens et al. | |
| 2006/0154198 A1* | 7/2006 | Durbin et al. | 433/29 |
| 2007/0172101 A1 | 7/2007 | Kriveshko et al. | |
| 2007/0172112 A1 | 7/2007 | Paley et al. | |
| 2008/0199829 A1 | 8/2008 | Paley et al. | |

FOREIGN PATENT DOCUMENTS

| | | |
|---|---|---|
| EP | 0837659 B1 | 11/1999 |
| EP | 1 650 529 A1 | 4/2006 |
| WO | WO-0008415 A1 | 2/2000 |
| WO | WO 2004/044787 A2 | 5/2004 |
| WO | WO-2004/100067 | 11/2004 |

OTHER PUBLICATIONS

European Search Report, 62701EP011, PCT/US2007/001652, May 11, 2010.

Rusinkiewicz, et al., "Real-Time 3D Model Acquisition", http://www.cs.princeton.edu/~smr/papers/rt_model, (2002).

"International Search Report", PCT/US2007/001547, (Jul. 2, 2007), 1-3.

"International Search Report", PCT/US2007/001652, (Jun. 25, 2007),all.

"International Search Report", PCT/US2007/001396, (Jul. 23, 2007),all.

"Digital impressions: eliminating the weak link", *Lab Management Today*, (Jan. 2006),20 et seq.

Koidisa et al., 3D Visualization of Dental Data for Virtual Treatment Planning, 2004.

Williams et al., Technique for fabricating patterns for removable partial denture frameworks using digitized cases and electronic surveying, Jan. 2004, The Journal of Prosthetic Dectistry, vol. 91, Issue 1, pp. 85-88.

Xia, James et al., "Three-Dimensional Virtual-Reality Surgical Planning and Soft-Tissue Prediction for Orthognathic Surgery." IEEE Transactions on Information Technology in Biomedicines. Jun. 2001. vol. 5, Issue 2, pp. 97-107.

\* cited by examiner

VISUAL FEEDBACK OF 3D SCAN PARAMETERS

RELATED APPLICATIONS

This application claims the benefit of commonly-owned U.S. Prov. App. No. 60/761,078 filed on Jan. 20, 2006, the entire contents of which are incorporated by reference.

BACKGROUND

1. Field of the Invention

The invention relates to three-dimensional data acquisition and more particularly to uses of superposition as a visualization techniques to aid in capture and refinement of three-dimensional data.

2. Description of the Related Art

A wide range of techniques exist for acquiring three-dimensional data from a subject. These techniques range from active techniques that actively control an imaging stimulus such as structured laser illumination, x-rays, ultrasound, or magnetic resonance) to passive techniques that operate directly on video data captured from one or more cameras. One broad category of techniques employs continuous scanning in which incremental three-dimensional data is acquired and assembled into a full three-dimensional model.

In this latter category, regardless of the particular sensing technology, a scanning process can be divided into abstract steps of incremental data capture, incremental derivation of three-dimensional data, and registration of the incremental data to a common coordinate system. The final registration step brings the incremental data together into a single three-dimensional model of a scan subject.

Current techniques generally separate acquisition from registration, with registration being performed in a post-processing step separate from data acquisition. While this permits relatively exhaustive processing, it poses a significant disadvantage because accuracy and completeness of the overall scan cannot be evaluated until after the scan has been completed. Unrecoverable errors or gaps in incremental data cannot be identified and fixed without initiating a new scan, possibly a full scan to completely replace the defective results. In commercial applications, where scheduling a common time and location for a scan subject and scanning hardware may pose logistical difficulties, this may increase the effective cost of scanning and inconvenience any parties involved.

In certain instances, this difficulty may be addressed by using robotics, independent references, or other techniques to determining the position of a scanning device within a global coordinate system. In addition to imposing further equipment costs, this approach can only be used to continue a previous scan if the subject of the scan has retained its position and orientation within the same global coordinate system.

There remains a need for real time visual feedback systems to support continuous three-dimensional scanning. There also remains a need for improved guidance and visual feedback systems for use with particular three-dimensional imaging applications, such as digital dentistry.

SUMMARY

The systems and methods disclosed herein provide visual feedback concerning one or more scanning parameters to a user during acquisition of a three dimensional scan.

BRIEF DESCRIPTION OF THE FIGURES

The invention and the following detailed description of certain embodiments thereof may be understood by reference to the following figures.

DETAILED DESCRIPTION

The following description relates to an array of visual feedback techniques to assist in acquiring and analyzing three-dimensional data. While the description emphasizes continuous scanning and dental applications, it will be appreciated that the inventive concepts disclosed herein are not limited to the specific embodiments disclosed. For example, the dental visualization systems described herein may be supported by any imaging technology capable of capturing three-dimensional dental data of suitable precision and detail. Similarly, the diagnostically oriented techniques disclosed herein, such as analysis of surface preparations or occlusion of arches, may be useful deployed in other contexts, including medical applications, three-dimensional animation modeling, custom, rapid manufacturing processes, and so forth. In addition, while numerous combinations and variations of imaging technologies and dental applications are described, it will be appreciated that other combinations of the specific scanning, processing, and visualization techniques described herein may be used, and that such variations are intended to fall within the scope of this disclosure.

In the following description, the term "image" generally refers to a two-dimensional set of pixels forming a two-dimensional view of a subject within an image plane. The term "image set" generally refers to a set of related two dimensional images that might be resolved into three-dimensional data. The term "point cloud" generally refers to a three-dimensional set of points forming a three-dimensional view of the subject, such as might be reconstructed from a number of two-dimensional views. In a three-dimensional image capture system, a number of such point clouds may also be registered and combined into an aggregate point cloud constructed from images captured by, for example, a moving camera. Thus it will be understood that pixels generally refer to two-dimensional data and points generally refer to three-dimensional data, unless another meaning is specifically indicated or otherwise clear from the context.

The terms "three-dimensional surface representation", "digital surface representation", "three-dimensional surface map", and the like, as used herein, are intended to refer to any three-dimensional surface map of an object, such as a point cloud of surface data, a set of two-dimensional polygons, a particle system, or any other renderable primitives or other data representing all or some of the surface of an object, as might be obtained through the capture and/or processing of three-dimensional scan data, unless a different meaning is explicitly provided or otherwise clear from the context.

A "three-dimensional representation" may include any of the three-dimensional surface representations described above, as well as volumetric, vector, and/or other representations, unless a different meaning is explicitly provided or otherwise clear from the context.

In general, the terms "render" or "rendering" refer to a two-dimensional visualization of a three-dimensional object, such as for display on a monitor. However, it will be understood that stereoscopic, three-dimensional, and other rendering technologies exist, and may be usefully employed with the systems and methods disclosed herein to render objects in three dimensions. As such, rendering should be interpreted broadly unless a narrower meaning is explicitly provided or otherwise clear from the context.

The term "dental object", as used herein, is intended to refer broadly to subject matter specific to dentistry. This may include intraoral structures such as dentition, and more typically human dentition, such as individual teeth, quadrants, full arches, pairs of arches which may be separate or in various types of occlusion, soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture which may not be intraoral structures as described above, such as dental models (full and/or partial), wax-ups, investment molds, and the like, as well as trays, bases, dies, and other components employed in the fabrication of restorations, prostheses, and the like. Dental objects may be categorized in a number of ways. For example, dental objects may be categorized as natural dental objects such as the teeth, bone, and other intraoral structures described above and artificial dental objects such as the restorations, prostheses, appliances, hardware, and interim components of dental manufacture as described above. Similarly, dental objects may be categorized intraoral dental objects (which may be natural or artificial) and extraoral dental objects (which are generally but not exclusively artificial).

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified or otherwise clear from the context, the term "model", when used alone, may refer to either or both of a physical model and a digital model.

Figure 1:
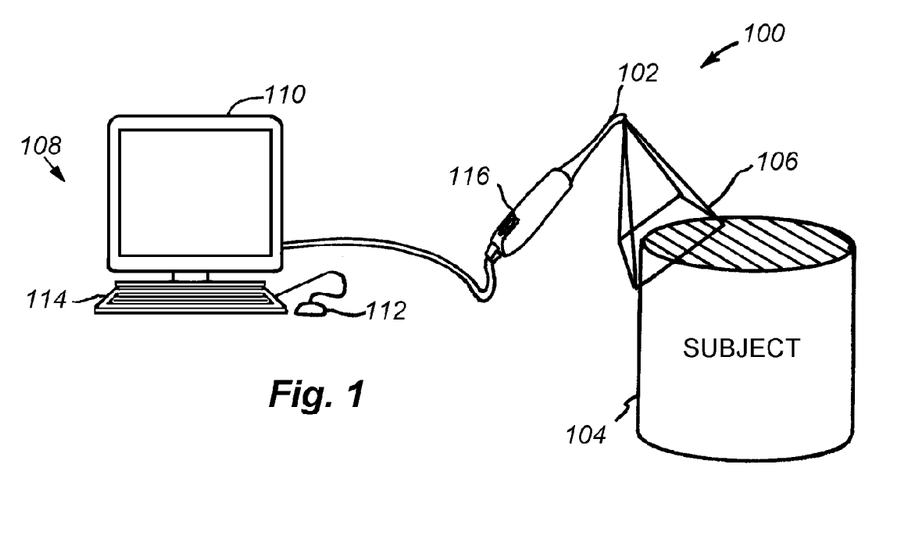
FIG. 1 shows a dental image capture system.

FIG. 1 shows an image capture system. In general, the system 100 may include a scanner 102 that captures images of a subject 104 within an image plane 106, and forwards the images to a computer 108, which may include a display 110 and one or more user input devices such as a mouse 112 or a keyboard 114.

The scanner 102 may include any camera or camera system suitable for capturing images from which a three-dimensional point cloud may be recovered. For example, the scanner 102 may employ a multi-aperture system as disclosed, for example, in U.S. Pat. Pub. No. 20040155975 to Hart et al., the entire contents of which is incorporated herein by reference. While Hart discloses one multi-aperture system, it will be appreciated that any multi-aperture system suitable for reconstructing a three-dimensional point cloud from a number of two-dimensional images may similarly be employed, including systems with moving apertures, fixed apertures, and/or electro-mechanically shuttered apertures. In one multi-aperture embodiment, the scanner 102 may include a plurality of apertures including a center aperture positioned along a center optical axis of a lens and any associated imaging hardware. The scanner 102 may also, or instead, include a stereoscopic, triscopic or other multi-camera or other configuration in which a number of cameras or optical paths are maintained in fixed or moving relation to one another to obtain two-dimensional images of an object from a number of slightly different perspectives. The scanner 102 may include suitable processing for deriving a three-dimensional point cloud from an image set or a number of image sets, or each two-dimensional image set may be transmitted to an external processor such as contained in the computer 108 described below. In other embodiments, the scanner 102 may employ structured light, laser scanning, direct ranging (e.g., time of flight in a known direction), or any other technology suitable for acquiring three-dimensional data, or two-dimensional data that can be resolved into three-dimensional data.

In one embodiment, the scanner 102 is a handheld, freely positionable probe having at least one user input device, such as a button, lever, dial, thumb wheel, switch, or the like, for user control of the image capture system 100 such as starting and stopping scans. In an embodiment, the scanner 102 may be shaped and sized for dental scanning. More particularly, the scanner may be shaped and sized for intraoral scanning and data capture, such as by insertion into a mouth of an imaging subject and passing the imaging plane 106 over one or more intraoral structures at a suitable distance to acquire surface data from teeth, gums, and so forth. The scanner 102 may, through such a continuous acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthetic, to ensure proper fitting using a previous scan of corresponding dentition, such as a tooth surface prepared for the prosthetic.

Although not shown in FIG. 1, it will be appreciated that a number of supplemental lighting systems may be usefully employed during image capture. For example, environmental illumination may be enhanced with one or more spotlights illuminating the subject 104 to speed image acquisition and improve depth of field (or spatial resolution depth). The scanner 102 may also, or instead, include a strobe, flash, or other light source to supplement illumination of the subject 104 during image acquisition. In other structured light systems, the illumination may be in the form of an array of laser beams that form a pattern on a surface, which pattern may be employed to recover three-dimensional data from the surface. Other systems employ a single laser beam along with directional information to gather point-by-point direction and range information. All such imaging systems may be usefully employed to acquire three-dimensional data as described herein.

The subject 104 may be any object, collection of objects, portion of an object, or other subject matter. While illustrated in FIG. 1 as a simple geometric form, the subject 104 may include much more complex surfaces, and any number of separate elements. For example, in a dental imaging application, the subject 104 may include a tooth, a quadrant of teeth, or a full collection of teeth including two opposing arches from which a virtual dental impression is desired. The subject 104 may also, or instead, include a dental prosthesis such as an inlay, a crown, or any other dental prosthesis, implant, or the like. The subject 104 may include a dental model, such as a plaster cast, wax-up, impression, or negative impression of a tooth, teeth, soft tissue, or some combination of these. An optical or textured imaging agent may optionally be applied to surfaces of the subject 104 to improve capture of three dimensional points. In other embodiments, the subject 104 may be a human head, or a portion thereof, from which a three-dimensional model may be acquired for custom fitting of a hearing aid, eyeglasses, goggles, or the like. In other embodiments, the subject 104 may be a physical model of an object for use in digital animation, such as a miniature, physical model for use in a three-dimensional digital animation process. From the preceding examples, it will be apparent that a system using the techniques described herein may be suitably adapted to a wide range of applications for relatively short range, high resolution three-dimensional image acquisition. However, one skilled in the art will appreciate that suitable adaptations to the image capture system 100 may be made for a variety of other three-dimensional imaging applications based upon multi-aperture or multi-camera systems, as well as other three-dimensional imaging systems and technologies, and all such variations are intended to fall within the scope of this disclosure.

The image plane 106 may include a two-dimensional field of view of the scanner 102. It will be appreciated that the term "image plane" as used in this paragraph, refers to a plane in the imaging environment rather than a plane within an optical sensor (such as film or sensors) where an image is captured. Though illustrated as a rectangle the image plane 106 may, for example, form a square, a circle, or any other geometry provided by the scanner 102. In general, the scanner 102 will have a depth of field or range of depth resolution that, together with the field of view 106, specifies a measurement volume of the scanner 102. The depth of field may vary with environmental conditions such as lighting (ambient or artificial), the texture or optical properties of the imaging subject, and so forth. It will further be understood that the term "field of view", as used herein may refer to a two-dimensional field such as an internal plane within the optics of an imaging system, an external plane such as a field in an imaging environment, or a region in a display, or may refer to a three-dimensional region such as a current measurement volume in an imaging environment. Thus, "field of view" as used herein should be interpreted in the broadest sense possible, unless a more specific meaning is explicitly provided, or otherwise clear from the context.

The computer 108 may be, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. This system may be operated to capture approximately 1,500 points per image set in real time using the techniques described herein, and store an aggregated point cloud of over one million points. As used herein, the term "real time" means generally with no observable latency between processing and display. In a video-based scanning system, real time more specifically refers to processing within the time between frames of video data, which may vary according to specific video technologies, but may generally be considered to fall between about ten frames per second and about thirty frames per second for many of the applications described herein. More generally, processing capabilities of the computer 108 may vary according to the size of the subject 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110.

Communications between the computer 108 and the scanner 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, ultrasound or other wireless communication medium. In medical imaging or other sensitive applications, wireless image transmission from the scanner 102 to the computer 108 may be secured. The computer 108 may generate control signals to the scanner 102 which, in addition to image acquisition commands, may include conventional camera controls such as focus or zoom.

In an example of general operation of a three-dimensional image capture system 100, the scanner 102 may acquire two-dimensional image sets at a video rate while the scanner 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. One useful example of such a technique is described in commonly-owned U.S. application Ser. No. 11/270,135, filed on Nov. 9, 2005, the entire contents of which is incorporated herein by reference. However, it will be appreciated that this example is not limiting, and that the principles described herein may be applied to a wide range of three-dimensional image capture systems. It will also be understood that terms such as "video" or "video rate" imply a wide range of possible frame rates associated with such video. While most modern video formats employ a frame rate of 25 to 30 frames per second, early video employed frame rates as low as 8 frames per second, and movies of the early 1900's varied from 12 to 18 frames per second. In addition, it is common for specialized imaging equipment to employ a rate adapted to the computational demands of particular imaging and rendering techniques, and some video systems operate with frame rates anywhere from 4 frames per second (for computationally extensive imaging systems) to 100 frames per second or higher (for high-speed video systems). As used herein, the terms video rate and frame rate should be interpreted broadly. Notwithstanding this broad meaning, it is noted that useful and visually pleasing three-dimensional imaging systems have been constructed according to the foregoing with frame rates of at least ten frames per second, frame rates of at least twenty frames per second, and frame rates between 25 and 30 frames per second.

It will be appreciated that the ability of certain systems, such as multiaperture camera systems, to derive three-dimensional data from two-dimensional video image sets may depend in part on an ability to establish correspondence of surface points between image pairs (or triplets, and so on). The process of establishing point correspondences may be improved by identifying, within the processing system, unique features of the surface upon which correspondence may be based. In certain aspects, distinguishing features of teeth at varying levels of detail may be employed to enhance this process. However, this process depends on an ability to locate such distinguishable features. The process of establishing point correspondences may also, or instead, be enhanced by the addition of optically detectable features thereto, which may be as simple as artificial black dots distributed over a white or relatively light surface. In a dental context, this may be achieved with a spray, powder, mouth rinse, or the like that distributes optically detectable matter across the dentition or other dental object to be scanned. By randomly distributing such small, distinguishable dots across the surface, the likelihood of locating distinguishable features in a particular image set may be significantly improved, thus improving the speed and accuracy of the overall three-dimensional data acquisition process.

From time to time in continuous or incremental data acquisition systems, the fitting or stitch between two frames may fail for reasons described in greater detail below. In such situations, a user may be notified through visual feedback that a recover mode has been entered. In the recover mode, the system 100 may seek to reacquire the previous scan by test fitting new scan data to previously acquired data, and providing visual feedback to a user to assist in navigating back to a scan location on the subject where the re-acquisition is being attempted. In a related landing mode, a user may attempt to initiate a new scan registered or connected to an existing three-dimensional model. Similar visual feedback tools may be provided to guide a user to an appropriate scan location, and notify a user when the scan has been reacquired. These techniques are described in greater detail in commonly-owned U.S. application Ser. No. 11/383,623, filed on May 16, 2006, incorporated herein by reference in its entirety. Other suitable techniques may be employed for navigation, controlling scan quality, analyzing scanned subject matter, and manipulating scanned models, various embodiments of which are described in greater detail below.

The display 110 may include any display suitable for video or other rate rendering at a level of detail corresponding to the acquired data or a rendered version of the acquired data. Suitable displays include cathode ray tube displays, liquid crystal displays, light emitting diode displays, plasma displays, and the like. In some embodiments, the display may include a touch screen interface using, for example capacitive, resistive, or surface acoustic wave (also referred to as dispersive signal) touch screen technologies, or any other suitable technology for sensing physical interaction with the display 110. In addition, where three-dimensional visualization is desired, the display 110 may include a three-dimensional display using a wide variety of techniques including stereo pair imaging, holographic imaging, and multiplanar or volumetric imaging, each with a number of rendering modalities that may be usefully employed with the systems described herein.

Figure 2:
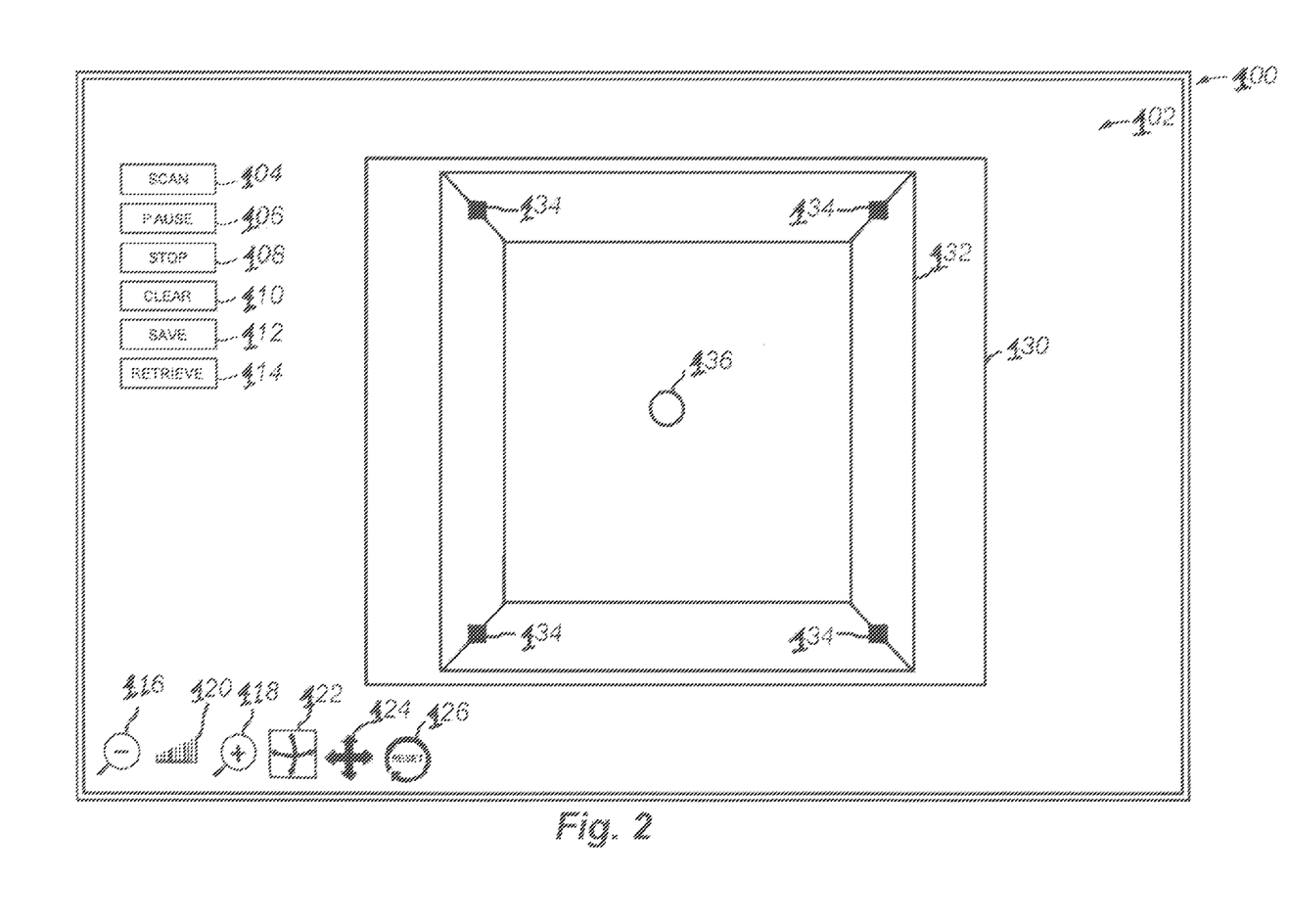
FIG. 2 depicts a view of a user interface for an image capture system.

FIG. 2 depicts a view of a user interface for an image capture system. The user interface 200 may include a window 202 rendered on a monitor such as the display 110 of FIG. 1. Within the window 202, a video image may be displayed including a measurement volume of a scanner, such as the image plane 106 of the scanner 102 of FIG. 1. Within the field of view or measurement volume, a video or other image of a subject such as the subject 104 of FIG. 1 may be displayed. However, as depicted in FIG. 2, no image acquisition steps have been initiated, so the window 202 remains blank except for various controls which will be described below.

Scanning controls may include, for example, a scan control 204, a pause control 206, a stop control 208, a clear control 210, a save control 212, and a retrieve control 214. The scan control 204 may initiate a three-dimensional scan. The pause control 206 may temporarily discontinue a scan in a manner that permits subsequent reacquisition of a continuous scanning process. The paused scan may exhibit a number of visual properties. For example, the video image may be frozen, or the video image may continue to display current video information while a point cloud or other scan data remains frozen, or the screen may go entirely blank, or some combination of these, all according to user preferences or a particular implementation. In general, a paused scan may remain active so that a user may resume the scan. By contrast, if a user activates the stop control 208, the scan may be terminated, such that a user would have to retrieve the scan, such as using the retrieve control 214 in order to continue adding data thereto. The save control 212 may store a scan and any related data for subsequent use. These controls may operate as buttons that a user activates to perform the indicated function, such as through a mouse click or, where the display 110 is a touch-screen, by direct physical interaction with the display 110. It will be appreciated that activation of the control may create a pop-up window, or provide drop down lists, radio buttons, text input fields, and any other controls suitable for parameterizing the particular selection. Thus for example, where a user activates the save control 212, a text box may appear for a user to enter a filename, directory or path information, and the like for saving any related data. Numerous techniques for organizing user interfaces and providing controls within a user interface are known in the art, and may be suitably adapted to the interface 200 described herein.

A number of navigation controls may be provided, such as a zoom out control 216, a zoom in control 218, a zoom indicator 220, a rotate control 222, a pan control 224, and a reset control 226. These controls may be used to view an acquired three-dimensional representation after a scan has been completed or, where a pause/resume feature is provided, during a scan. The reset control 226 may, for example, restore a view of a three-dimensional representation to a global coordinate system, or to a most recent view from which data was acquired during a scan.

A number of range finding visualizations may also be included that provide visual cues related to one or more scanning parameters of an image capture system. These visualizations may be rendered in real time, e.g., at the video rate of the image capture system, to provide real time user feedback and guidance with respect to proper orientation and positioning of a scanner during a scan. The user feedback may improve the quality and speed of data acquisition, particularly during continuous scanning operations that acquire a full three-dimensional representation of a subject as a sequence of fitted three-dimensional surface samples. These visual cues may be particularly useful in continuous three-dimensional data acquisition systems based upon camera motion estimation or similar techniques. In such techniques, sequential frames of data are registered to one another using various processing techniques such as those described in commonly owned U.S. application Ser. No. 11/270,135, filed on Nov. 9, 2005. This works well provided three-dimensional data can be successfully resolved from each sequential frame of image data, and there is sufficiently small displacement of the scanner that the data from sequential frames overlaps in three-dimensional space. However, when this "stitching" of sequential frames is lost, such as due to an operator moving outside the proper scanning distance, it can be very difficult to recover the continuous acquisition. Visualization tools that guide a user toward maintaining proper scanning distance advantageously promote a continuous, uninterrupted acquisition of three-dimensional data for an entire surface of interest.

For example, within a window 230 that shows a current video image from the image plane 106 of the scanner 102 (which is blank in FIG. 2, as the system has not started a scan), a volume 232 of space, such as the box depicted in FIG. 2, for which quality scan data can be captured may be depicted in perspective. This volume 232 rendered within the imaging space may assist a user in positioning subject matter within the video image appropriately for data acquisition. In addition, sliders 234 may be animated along z-axis edges of the volume 232 to indicate a distance of points of three-dimensional data actually being acquired. This may be based on, for example, a mean distance of some or all of the points, a distance of a central point, a range of distances for all or some of the points, or a distance of a point at each respective corner of the volume 232, such that the sliders 234 may move independently from one another during a scan. Distance calculations may be based on a current frame of image data, i.e., the most recently acquired data set, or an average of a predetermined number of immediately prior data sets, or upon all three-dimensional points of the three-dimensional surface representation falling within the volume 432 without regard to when they were acquired.

As another example, a dynamic object 236 such as a sphere or bullseye may be rendered in the center of the window 230. The dynamic object 236 may also, or instead, be positioned at another location within the window; however positioning the dynamic object 236 within the center of the window 230 advantageously permits a user to receive visual feedback from the dynamic object 236 without looking away from current video of the subject being scanned.

A number of useful animations may be provided by the dynamic object 236 to give user feedback to an operator of the image capture system 100. In one implementation, the dynamic object 236 may be an animated bullseye that is color-coded to provide distance information. The bullseye may, for example be rendered as concentric tings of different colors, such as red, white, and blue, with the central color filling the entire bullseye when a subject is properly distanced from the scanner. When the scanner moves too far from the subject, a red ring may form around the white circle filling a greater portion of the bullseye as the scanner moves further from a subject until the entire bullseye is completely red. Conversely, when the scanner moves too close to a subject, a blue circle may appear within the center of the white circle and grow in size as the scanner moves closer to the subject until the entire circle is blue. In this manner, a user may receive continuous feedback with respect to scan distance—a growing blue central circle as the scanner moves too close, and an engulfing red ring when as the scanner moves too far away—so that the scanner may maintain a proper distance from the subject for continuous acquisition of three-dimensional data in a three-dimensional representation of the subject. One useful model for rendering such a dynamic bullseye employs three co-axial cones of different colors, where the bullseye renders a planar cross-section of the three co-axial cones perpendicular to the common axis, and at a point along the common axis selected according to relative range from the subject In another example of animation, three concentric rings may be continuously displayed within the bullseye, with the radius of each ring independently controlled in proportion to the number of points that are too close, properly distanced, and too far. In another possible animation, the center ring (a circle) may move within the bullseye with an offset corresponding to an x-y displacement in the field of view or measurement volume of a region of the surface having the greatest density of points at a target, or desirable, scanning distance. Of course, it will be appreciated that the selection of colors for such animations is somewhat arbitrary, although significant contrast in hue or intensity may assist a user in recognizing deviations from an optimal scan distance.

Other visual cues and/or metaphors may also, or instead, be employed, such as a visualization of a plane passing through a sphere, active distance bars, animated text, or other visualizations, any of which may provide animated, visual feedback based on, for example, mean distance, center distance, or some other metric that can be derived from scanner output. More generally, visual cues may provide feedback concerning any scanning parameter such as depth of optimal data acquisition, width of field of view, rate of travel or yaw of the scanner 102, density of data acquisition, and so forth, as well as various combinations of these. These visual cues may provide graduated feedback to assist a user in maintaining proper scan distance, and to inform a user when a scan has been lost.

Figure 3:
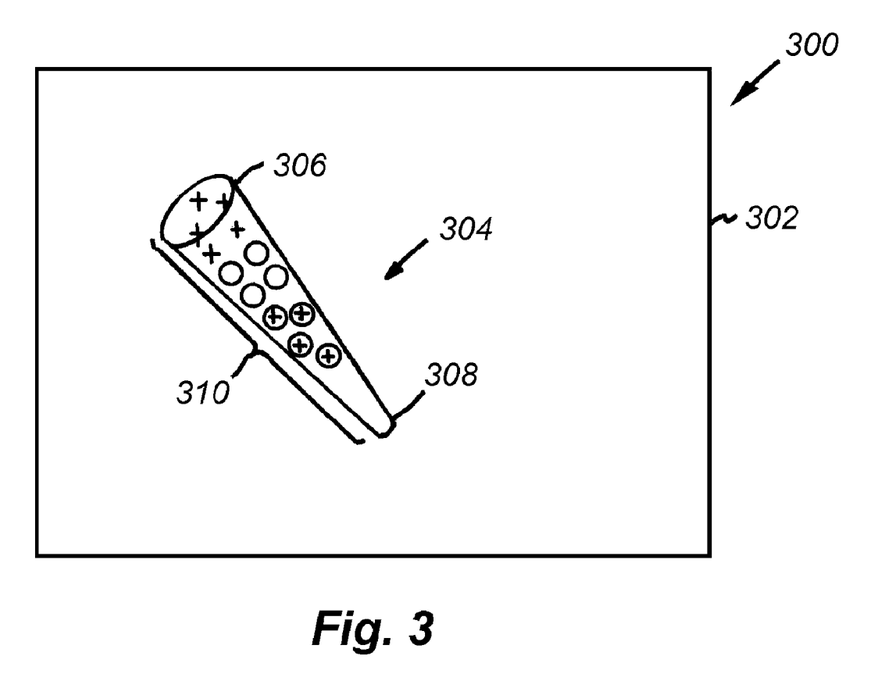
FIG. 3 depicts a view of a user interface for an image capture system.

FIG. 3 depicts a view of a user interface for an image capture system. This abstracted drawing shows a window 302 of the user interface 300, which may be, for example, the window 230 of FIG. 2, without the visual cues described therein. The window 302 may include a video image from a point of view of a scanner such as the image plane 106 of the scanner 102 described above with reference to FIG. 1. Within the window 302, the video image may include a subject 304. As depicted in FIG. 3 (and not by way of limitation), the subject 304 is a slender cylinder extended from a near end 306 relatively close to the scanner to a distant end 308 relatively far from the scanner. During a continuous surface scan of the subject 304, three-dimensional surface data may have been acquired, as indicated generally by x's, o's, and encircled +'s. Within the window 302, the three-dimensional surface scan may be rendered from the point of view of the scanner, along with shading or other visual effects to indicate shape and surface contours. The rendered three-dimensional surface scan may be superimposed in a registered fashion directly over the video image (or conversely, the video image may be superimposed on the rendered three-dimensional surface). This superposition alone provides significant user information, such as what surface regions of the subject 304 have been scanned. In addition, the rendered three-dimensional surface scan may be color-coded or otherwise rendered to provide color information concerning, for example, what region is currently being scanned in the continuous data acquisition process, what regions are too close to acquire scan data from, what regions are at a proper distance for acquisition of surface data, and what regions are too far for surface data. For example, if points on or near the near end 306 of the subject 304 are too close to acquire scan data—these points are indicated in FIG. 3 as x's—they may be rendered in a first color. Points at an optimal scanning distance—indicated in FIG. 3 as o's—may be rendered in a second color. Points too distance for acquisition of three-dimensional data—indicated in FIG. 3 as encircled +'s—may be rendered in a third color. Of course, this distance information may not be directly relevant because the rendered points have already been acquired in three-dimensional space. However, this color coding of the surface of the subject 304, as rendered through the acquired three-dimensional digital surface representation, may provide useful information to a user concerning the distance of the subject 304, particularly with respect to regions of the subject 304 that have not yet been scanned.

It will be appreciated that, while only a dozen or so points have been drawn in FIG. 3, a practical image capture system for use in dentistry and similar applications may require spatial resolution on the order of 100 microns or less for sufficient detail to fabricate properly fitting dental objects. As such, the actual point cloud acquired by the image capture system for a subject such as a dental arch may contain thousands, tens of thousands, hundreds of thousands, or millions of individual three-dimensional points, or more. While the small number of points illustrated in FIG. 3 is intended to assist in explaining the nature of a point cloud distribution and various rendering techniques applicable thereto with reference to the specific points shown (the x's, o's, and encircled x's), the larger number of points available in a typical scan can provide significantly improved visualization of surface contours and the like. It should also be appreciated that the points used to render the digital surface representation for display may include a subset of points in a full point cloud of acquired three-dimensional data, with the density of points selected according to any suitable design parameters including processing/rendering speed, need for contour visualization, and the like. It will also be understood that the data in the three-dimensional scan may be internally represented as points, particle systems, vectors, or any other suitable representation. Thus, while the data may be rendered as a point cloud of any desired density, this may or may not correspond to the internal representation of scan data. Further, the rendering may employ techniques other than point rendering, such as a polygonal mesh or the like, with suitable adaptations to the techniques described above for visualizing range, scan quality, and the like.

It will be appreciated that the capability of capturing highly detailed models of dental objects, and in particular, the capability of capturing highly detailed digital surface representations of dentition directly from an intraoral scan, enables an array of subsequent processing steps that may be useful to dentists, dental laboratory technicians, oral surgeons, and the like. A number of such applications are now described in greater detail.

The embodiments described in reference to FIG. 2 and FIG. 3 emphasize the use of an interface that displays a subject from a point of view of the scanner. However it will be understood that alternative models may be used, such as an interface that renders acquired data from a fixed point of view within a global coordinate system. In an approach employing a fixed point of view, the generally visualization strategy may change, such as by providing continues feedback as to the position of the scanner relative to the subject. However, the visual cues described above may generally be adapted to such an environment, or other environments, in a number of ways as will be readily appreciated by one of skill in the art.

In general, a system as described herein may have a number of operating modes, such as a file management mode, a model editing mode, a model evaluation and/or analysis mode, a scanning mode, and so forth. Two such modes are described with respect to FIGS. 4 and 5 below, which show a scanning mode and an evaluation mode respectively.

Figure 4:
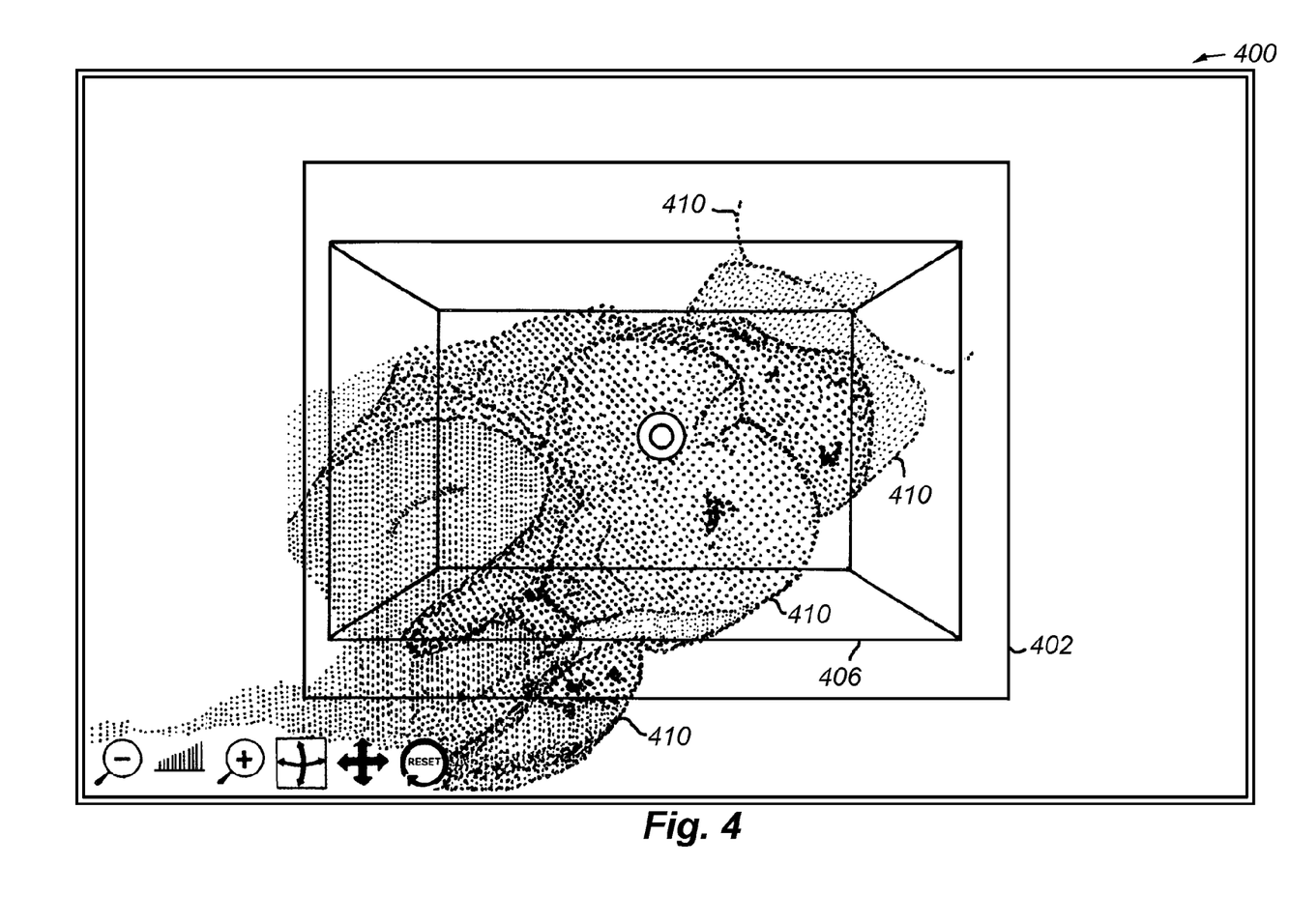
FIG. 4 depicts a view of a user interface for an image capture system during an acquisition of three-dimensional data.

FIG. 4 depicts a view of a user interface for an image capture system during an acquisition of three-dimensional data. The user interface 400 may include a window 402 including range-finding visual cues 404, 406, all as generally described above. Within the window 402, a video image may be displayed, such as a video image from a current point of view of a scanner, such as the scanner 102 described above. As depicted, the video image may include a plurality of teeth 410 and other intraoral structures visible during an intraoral scan. It will be noted that three-dimensional points acquired from the surface, i.e., the current digital surface representation, may be rendered within the user interface 400, and more particularly, may be rendered from the point of view of the scanner and superimposed on the current video image. Although not depicted, it will be understood that in other embodiments, the current digital surface representation may be rendered from a fixed point of view.

In addition to permitting visual enhancements such as contour shading and feature emphasis, the rendering may provide specific feedback to a user concerning the current scan. For example, regions too close for capture of scan data may include previously acquired points, which may be rendered in the window 402 with a style or color that indicates their relative proximity to the scanner. Conversely, regions of the intraoral structures too far for capture may also, or instead, include previously acquired points, which may be rendered in the window 402 with a style or a color that indicates their relative distance from the scanner. As new surface data is acquired and added to the digital surface representation, the new point data may concurrently, or in real time or near real time, be added to the rendered view of the digital surface representation. In this manner, a user may receive immediate visual feedback, such as the density of rendered points or relative fineness/coarseness of a polygonal mesh, with respect to whether data is being successful acquired from surfaces visible within the window 402. This information may indicate gaps in surface data so that a user can back up and rescan surfaces of the subject for which data has not been captured, or for which inadequate or defective data has been captured. This feedback may in part flow directly from the process of rendering an increasing number of points within the window as new surface data is acquired. The visual feedback may also, or instead, be supplemented by rendering points with a density in the window 402 specifically selected to communicate to a user whether adequate data has been acquired from within the current view. While specific feedback examples are noted above, it will be understood that more generally, numerous and various uses of brightness, texture, shading, color, and/or rendered point cloud density, or the like may be employed to provide visual feedback to a user concerning scan quality, detail, and the like.

The visual metaphor may be one of spray painting the video image with a shaded surface map as points are acquired. The point cloud of the digital surface representation (or other representation) may be rendered as a growing constellation of points that forms over the video subject matter as data is acquired. Regions for which a target point density has been achieved may, for example appear as continuous surfaces, while regions with inadequate surface data may be rendered as discrete points having visible gaps therebetween, which gaps may be varied in size according to, e.g., the density of point data in the underlying digital surface representation. As another example, points may be rendered as uniformly spaced surface points, which may be color coded according to density of point data in the underlying digital surface representation.

In certain embodiments, the acquired digital model may be compared to a statistical, spatial, or other model of expected shapes relevant to dentistry (or other objects, for non-dental applications), using know machine vision and other techniques. This may include relatively subtle variations such as unexpected tooth contours, thicknesses, or the like, as well as gross deviations that are likely a result of user or equipment malfunction or loss of scan data. Where deviations from expectations are detected, these may be visually identified within the window 402 through use of color, shading, and other cues and annotations described generally above. Thus, algorithmically unexpected scan results may be immediately flagged during a scan for any suitable human intervention (which may, of course, be none where the unexpected feature is known by the operator to actually be present).

Figure 5:
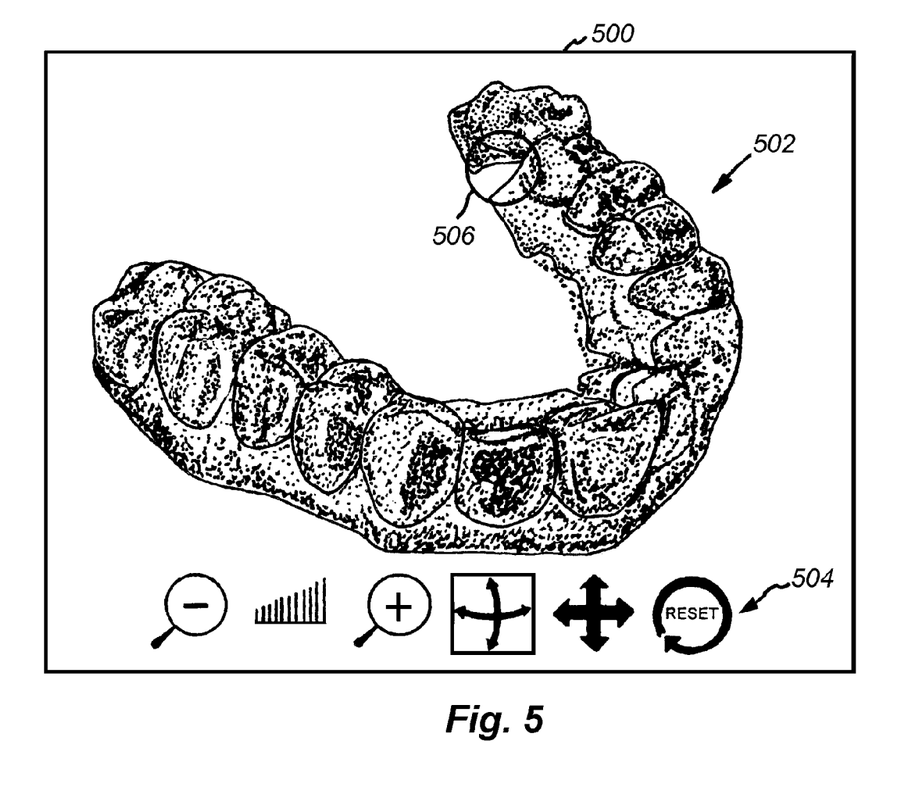
FIG. 5 depicts a view of a user interface for an image capture system during an evaluation.

FIG. 5 depicts a view of a user interface for an image capture system during an evaluation. The window 500 may include a two-dimensionally rendered perspective view 502 of a stored digital surface representation, as well as a number of navigation controls 504 and other user controls for viewing, manipulating, and evaluating the digital surface representation. As depicted in FIG. 5, the digital surface representation includes a full arch, although it will be appreciated that any three-dimensional surface may be stored as a digital surface representation, including portions of teeth, one or more full teeth, soft tissue, quadrants, arches, dental objects such as hardware, appliances, prosthetics, and interim components of dental manufacture, as well as, in non-dental applications, any other object or objects.

In the window, gross errors in a digital model, such as a region 506 of omitted or missing scan data, may be intrinsically identified by the absence of visible point data. Other errors such as excessive variability of surface data may be intrinsically identified by fuzziness or excessive random texture. Visualization of scan quality may also, or instead, be augmented by explicit indicators, such as coloring, shading, surface texturing, or any of the other visual cues described above, which may visually identify regions of incomplete scan data, inaccurate scan data, insufficient scan detail (such as where a restoration will be affixed) and the like.

Using the navigation controls 504, a user may rotate, pan, zoom in, or otherwise navigate around and within the digital model to more closely inspect areas of interest, or to view the model from a number of perspectives to visually inspect otherwise occluded features. One user control (not shown) may permit a user to return to data acquisition, e.g., the scanning mode of FIG. 4, to acquire additional data where a void or deviation is detected (either automatically or through human visual inspection). This control, or another control, may permit a user to select a specific point on the surface of the digital model (or the scan subject, although the distinction becomes trivial for highly detailed and accurate digital models) where the continuous scan is to be reacquired from the subject, as described for example in commonly-owned U.S. application Ser. No. 11/337,182, filed on Jan. 20, 2006, the entire content of which is incorporate herein by reference.

It will be appreciated that, while FIG. 5 depicts a two-dimensional rendering based upon a display of discrete surface points, other rendering techniques may be employed, such as a continuous surface map formed of polygons or other regular or irregular planar or non-planar surfaces. More generally, rendering may employ a polygonal mesh, point cloud, particle system, and/or other renderable primitive(s).

Figure 6:
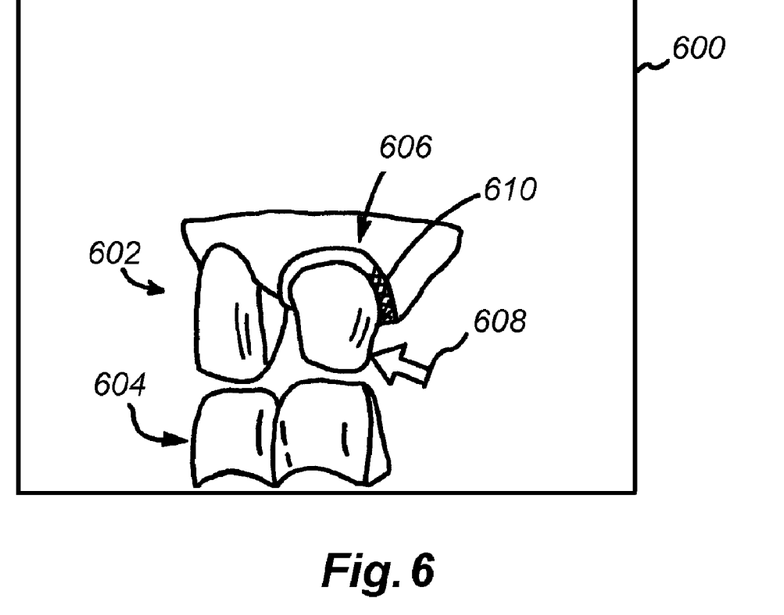
FIG. 6 depicts a dental model in digital form.

FIG. 6 depicts a dental model in digital form, otherwise referred to herein as a digital surface representation, a three-dimensional representation, or the like. The dental model may be rendered, for example within a window 600 of the user interface described above with reference to FIG. 2 from a three-dimensional point cloud captured in a continuous intraoral scanning process as described above with reference to FIG. 1. The user interface may be adapted for use by a dentist (or dental laboratory) to review a surface preparation for a crown as depicted in FIG. 6, or more generally to review any artificial or natural, intraoral or extraoral dental object for which a digital surface representation has been acquired. It will be understood that in this mode, new data is not being acquired. Rather, a stored model may be processed through a combination of user interaction and automated analysis controlled through the user interface.

In operation, a dentist may prepare a tooth surface for a crown using suitable dental tools. The dentist or a dental technician may then acquire a scan from the dental patient's mouth including the prepared surface and any surrounding or opposing tooth structures. The dentist may then specify in the user interface a restoration type such as a crown, a bridge, a veneer, an inlay, an onlay, or the like. After receiving the dentist's specification of restoration type, an automated process may examine the surface preparation and surrounding dentition to ensure adequate physical clearance, taper, appropriate shape, and the like for the specific restoration type. The automated process, which may be performed, for example, by the computer 108 described above, may generate corresponding annotations which may be visual annotations rendering within a display of the model, or textual annotations (which may, for example, be rendered within the display, rendered alongside the display in a separate window, or stored in a file) containing narrative description of conclusions, or a combination of these.

As depicted in FIG. 6, the three-dimensional representation of dentition may include including portions of two arches 602, 604 in occlusion (although the arches are in occlusion, there may be space between any pair of opposing teeth, as depicted in FIG. 4) and one surface 606 prepared for a crown. The portions of the arches 602, 604 may include single teeth, quadrants, full arches, or any other portions of one or more teeth or tooth surfaces useful for analyzing a crown surface preparation. It will also be understood that, while the arches are depicted in occlusion, the user interface may depict only one arch, or may depict the arches separated. Any automated analysis may be performed on the stored model, which may be manipulated to place the arches in occlusion, rather than the rendered model in the window, which may be in any configuration useful for display. After automated analysis, one or more regions may be highlighted with annotations or other visual cues such as an arrow 608 or surface effect 610 such as color, texturing, cross-hatching, or the like. For example, the arrow 608 may indicate a region of inadequate taper. As another example, the cross-hatched surface effect 610 may indicate an inadequate reduction of material at the butt joint margin. Other effects, such as use of different colors, different opacity, variations in brightness, or other surface treatment, different levels of surface detail or shading, highlighting, callouts, a trace or line around relevant regions, and so forth, may be similarly employed, either alone, or in combination with other effects. Within the interface, the annotations may be hyperlinked or otherwise active, so that a dentist may click on these annotations and receive narrative, reference materials, or other descriptive feedback. Where physical specifications for a particular restoration require additional removal, the regions to be removed may be depicted within the three-dimensional model using one or more visual cues for identification by the dentist. In certain embodiments, regions recommended for removal may include a number of different possible regions for removal, such as the surface preparation and/or an opposing tooth surface.

A process of preparing a tooth surface, scanning the tooth surface, and analyzing the tooth surface may be applied iteratively to refine a surface preparation. In an iterative process, a dentist may repeat steps of tooth removal and scanning until a satisfactory surface preparation is achieved.

It will be understood that correct specifications for a particular restoration may vary from dentist to dentist, from laboratory to laboratory, from manufacturer to manufacturer, and from tooth to tooth (e.g., anterior v. posterior crowns). For example, occlusion and clearance for incisal tooth surfaces may be analyzed differently from occlusion and clearance for molar occlusal surfaces. As another example, different dentists may have different preferences for tightness of fit for a prosthetic to a prepared tooth surface. These variations, whether dictated by context (e.g., particular teeth or a particular patient), objective criteria (e.g., manufacturing specifications), or subjective criteria (e.g., dentist preferences), may be accommodated by an automated analysis during an evaluation of a digital model so that resulting annotations or visualizations correspond correctly to a particular patient, dentist, and prescription.

The types of features in a specification may generally relate to features of the prepared surface such as taper (angling of prepared surfaces to accommodate placement of the prosthetic), draw path (taper, as well as physical clearance from neighboring dentition such as adjacent and opposing teeth), reduction of surfaces (to accommodate physical structure of prosthetic), clearance from opposing teeth, adequacy of margin, and so forth. Any features that can be objectively characterized, such as curvature, taper, clearance, and the like, can be tested for against an accurate three-dimensional representation of an actual surface preparation, with suitable visualizations generated to guide a dentist in improving or accepting a preparation. In certain cases, such as a bridge, multiple teeth must be prepared. The analysis described herein may include an analysis of draw path for the multi-tooth preparation that ensures a fit is physically possible. Thus, it will be appreciated that, more generally, analysis of a surface preparation may include a multi-tooth surface preparation for a single dental object.

While reviewing a crown surface preparation is one useful application of the analysis and visualization tool described above, it will be understood that the techniques above may be similarly applied to a variety of dental objects, including restorations, hardware, appliances, and the like, as well as any region of diagnostic or other significance that can be objectively characterized for automated analysis.

Figure 7:
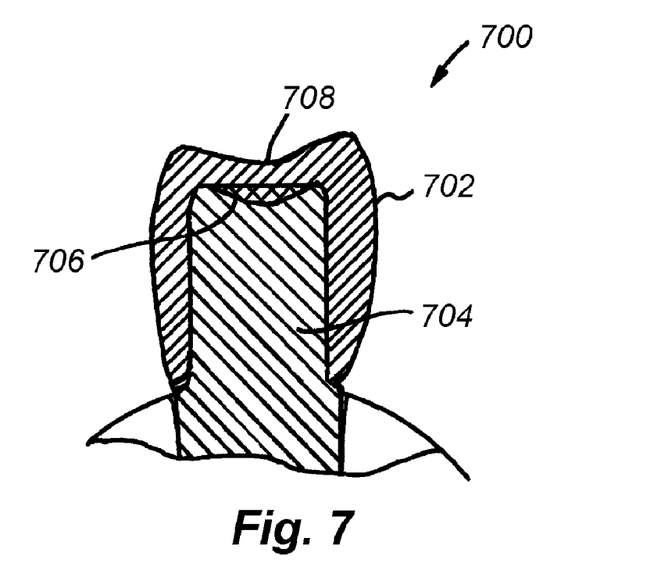
FIG. 7 depicts a cross-section of a digital dental model.

FIG. 7 depicts a cross-section of a digital dental model. The cross section 700 may be rendered within a window of a user interface, as described generally above. As a visualization tool, the user interface may permit a dentist to review a cross-section of the dental model to permit more accurate assessment of dimensions, orientation, and so forth. The user interface may also permit placement of a virtual prosthetic 702, in this case a posterior crown, onto the digital model 704. A collision 706 between the models, as depicted in FIG. 5 as an inadequate occlusal reduction under the deepest fossea pit 708 of the prosthetic 702, may be displayed in any manner, such as shading, coloring, brightness, texture, or mixing of cross-hatching styles for overlapped models.

Figure 8:
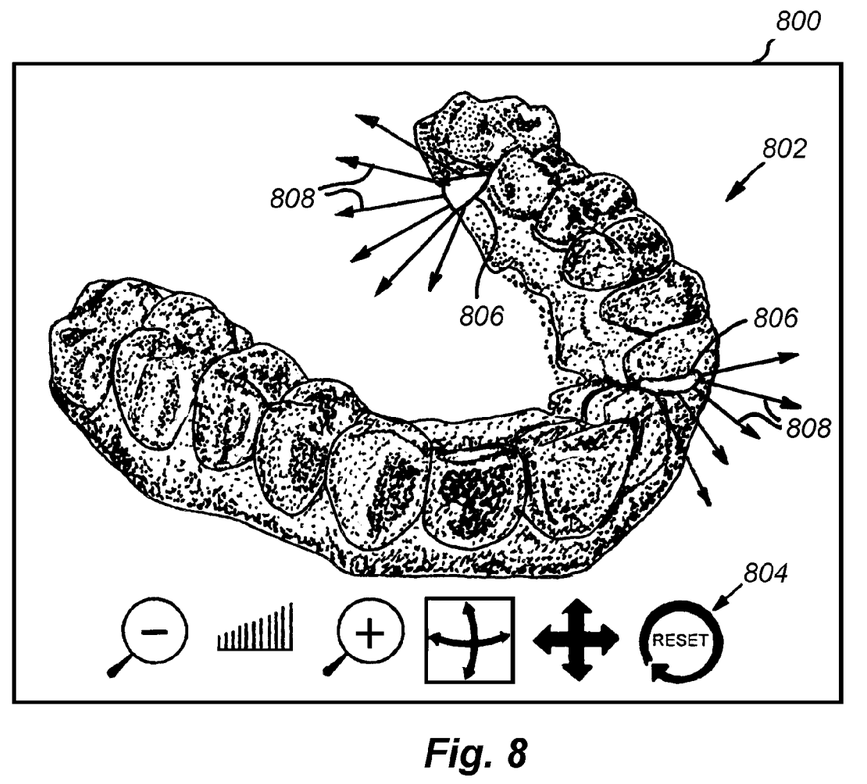
FIG. 8 depicts a visualization technique for locating holes in a digital surface representation of dental subject matter.

FIG. 8 depicts a visualization technique for locating holes in a digital surface representation of dental subject matter. A window 800 of a user interface, which may include any of the user interfaces described above, may include a two-dimensionally rendered perspective view 802 of a stored digital surface representation, as well as a number of navigation controls 804 and other user controls for viewing, manipulating, and evaluating the digital surface representation. As depicted in FIG. 8, the digital surface representation includes a full arch, although it will be appreciated that any three-dimensional surface may be stored as a digital surface representation, including portions of teeth, one or more full teeth, soft tissue, quadrants, arches, dental objects such as hardware, appliances, prosthetics, and interim components of dental manufacture, or various combinations of any of the foregoing, as well as, in non-dental applications, any other object or objects. The figure shows a visualization of gaps in surface data, which may be used, for example, in an analysis or evaluation mode of the image capture system.

As shown in FIG. 8, a hole 806 in the digital surface representation may be visualized by simulating an internal illumination of the digital model, with rays 808 of light passing through the hole. The visual effect may, for example, employ a flashlight or other metaphor to simulate internal illumination. The rays 808 may be depicted literally as lines, as shown in the figure, or as a glow emanating from the hole 806, or as a corresponding illumination of a dark background for the view 802, or as a combination of these. Other techniques for visualizing illumination may similarly be employed, such as shadows cast upon neighboring contours and surfaces of the digital model, and so forth. Any such techniques that simulate an internal illumination of the digital surface representation may be suitably employed to indicate the presence, size, and/or shape of holes in the surface data.

It will be appreciated that a hole is a relative concept, particularly for a digital surface representation formed from a set of discrete three-dimensional points. Holes may be identified, for example, as regions of relatively low point density, or a point density below a predetermined threshold, such as a density adequate for fabricating physical dental models or for performing dental diagnosis or requesting fabrication of a prosthetic. The threshold or other parameters used to identify holes may be user selected, so that data density may be controlled according to, for example, user preferences, desired scan speed, or an intended end use of the digital model. In addition, the threshold or parameters may be varied over the surface of the digital model, such as by requiring greater point density around a region of a surface preparation for a dental prosthetic.

Using the navigation controls 804, a user may rotate, pan, zoom in, or otherwise navigate around and within the digital model to more closely inspect areas of interest, or to view the model from a number of perspectives to visually inspect otherwise occluded features. One user control (not shown) may permit a user to return to data acquisition, e.g., the scanning mode of FIG. 4, to acquire additional data where a void or deviation is detected (either automatically or through human visual inspection). This control, or another control, may permit a user to select a specific point on the surface of the digital model (or the scan subject, although the distinction becomes trivial for highly detailed and accurate digital models) where the continuous scan is to be reacquired from the subject, as described for example in commonly-owned U.S. applicaion Ser. No. 11/337,182, filed on Jan. 20, 2006, the entire content of which is incorporated herein by reference.

Figure 9:
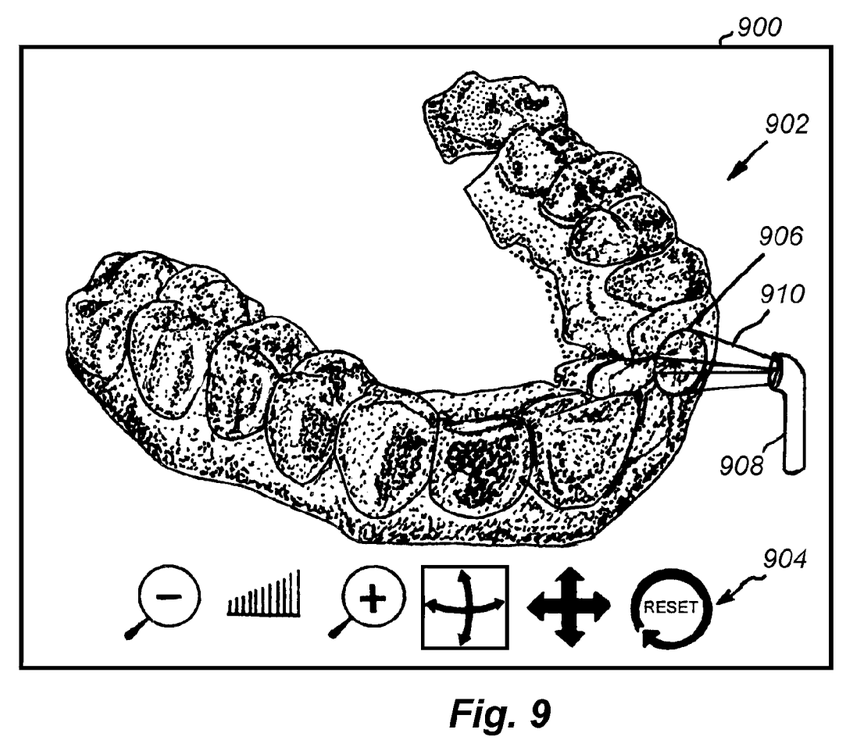
FIG. 9 depicts a visualization technique using a simulated external illumination.

FIG. 9 depicts a visualization technique using a simulated external illumination. A window 900 of a user interface, which may be any of the user interfaces described above, may include a two-dimensionally rendered perspective view 902 of a stored digital surface representation, as well as a number of navigation controls 904 and other user controls for viewing, manipulating, and evaluating the digital surface representation. As depicted in FIG. 9, the digital surface representation includes a full arch, although it will be appreciated that any three-dimensional surface may be stored as a digital surface representation, including portions of teeth, one or more full teeth, soft tissue, quadrants, arches, dental objects such as hardware, appliances, prosthetics, and interim components of dental manufacture, or various combinations of any of the foregoing, as well as, in non-dental applications, any other object or objects. The figure shows a visualization of external illumination of the model, which may be used, for example, in an analysis or evaluation mode of the image capture system.

As shown in FIG. 9, an illumination beam 910 may be visualized as emanating from a scanner 908 or other object within the window 900 and falling upon a region 906 of the view 902 of the digital model. An orientation and position of the scanner 908 may be controlled using the controls 904 within the window 900 of the user interface. The visual effect may be, for example, that of a flashlight or spotlight, or some other metaphor to simulate a beam of illumination external to the view 902 of the digital model. Rays 910 of illumination may be depicted literally as lines, as shown in the figure, or as a lighted beam emanating from the scanner 908, or as a corresponding illumination of a dark background for the view 902, or as a combination of these. Other techniques for visualizing illumination may similarly be employed, such as shadows cast upon the "illuminated" contours and surfaces of the digital model, and so forth. Any such techniques that simulate an internal illumination of the digital surface representation may be suitably employed.

The simulated external illumination beam may serve a number of purposes within the user interface. For example, in one scanning model where the view 902 remains fixed, the rays 910 of the illumination beam may be used during an acquisition of three-dimensional data to localize the scanner 908 with respect to the underlying physical model that is the subject of a scan. Thus, the simulated external illumination beam may serve as a navigational tool during a scan by providing visual feedback to a user concerning a location of the scanner with respect to a scan subject. A position and/or orientation of the scanner may be depicted within the interface for user feedback, so that a user knows a current location of the scanner 908. Also, or instead, an image of the scanner 908 rendered within the interface may include an illumination beam, line traces, or other visual effects to depict a current measurement volume for the scanner. In this model, or other models, the illuminated region 906 of the surface may correspond to a region from which data is being acquired. The illuminated region 906 may correspond, for example, to a field of view or measurement volume of the scanner 908. In other embodiments, the illuminated region 906 may correspond to a location selected for reacquiring a paused scan. This localization information may permit a selection of one or more corresponding frames of source scanner data to improve efficiency of a reacquisition process. That is, when reacquiring a scan, the reacquisition may be based on a localized search of surface data in a correct, or nearly correct, orientation. As a significant advantage, this type of visual cue reduces the need for the large computational overhead associated with a generalized registration process.

As noted above with reference to FIG. 8, a user may operate navigational controls, which may be in a user interface and/or physically located on a scanner to rotate, pan, zoom in, or otherwise navigate around and within the digital model to more closely inspect areas of interest, or to view the model from a number of perspectives to visually inspect otherwise occluded features. One user control (not shown) may permit a user to return to data acquisition, e.g., the scanning mode of FIG. 4, to acquire additional data where a void or deviation is detected (either automatically or through human visual inspection). This control, or another control, may permit a user to select a specific point on the surface of the digital model (or the scan subject, although the distinction becomes trivial for highly detailed and accurate digital models) where the continuous scan is to be reacquired from the subject, as described for example in commonly-owned U.S. application Ser. No. 11/337,182 filed on Jan. 20, 2006, the entire content of which is incorporated herein by reference.

Numerous additional visualization techniques may be employed with the systems and methods described herein including combinations of the specific techniques described above, as well as combinations of any one or more of the foregoing with additional technologies. By way of example, a second scanner such as a PMD[vision] camera from PMD Technologies may be employed to capture real-time, three-dimensional data on dynamic articulation and occlusion. While this scanner employs different imaging technology (time-of-flight detection from an array of LEDs) than described above, and produces results with resolution generally unsuitable for reconstruction of dental models, such a scanner may be employed to infer motion of, e.g., opposing dental arches with sufficient resolution to select an axis for articulation or otherwise capture dynamic information that can be applied to two or more rigid bodies of a dental object scan. In another aspect, the video-rate three-dimensional data from the second scanner may be employed to capture one or more reference points, which may be used to animate a rendering of highly detailed models or two or more rigid bodies, such as a detailed model of upper and lower arches as described generally above. Thus real-time animated rendering of relative motion may be provided for detailed models of rigid bodies, to provide a rendered view of relative motion for dental arches (or other bodies). This data may be supplemented with more precise alignment data statically captured from digital or manual bite registration to provide reference or calibration points for continuous, dynamic motion data. Thus in one aspect, there is disclosed herein a technique for capturing, storing, and or rendering dynamic motion data for dental arches using a first scanner to obtain a detailed three-dimensional representation of the dental arches and a second scanner to capture relative motion data that can be mapped to the detailed model from the first scanner.

It will be appreciated that the processes and methods disclosed above may be realized in hardware, software, or any combination of these suitable for the three-dimensional imaging and modeling techniques described herein. It will also be appreciated that the user interfaces, user interface controls, and methods of using same, as well as the visualizations, digital model processing and analysis, and rendering as described herein may similarly be expressed as methods or processes embodied in hardware, software, and various combinations thereof. This includes realization in one or more microprocessors, microcontrollers, embedded microcontrollers, programmable digital signal processors or other programmable devices, along with internal and/or external memory. The may also, or instead, include one or more application specific integrated circuits, programmable gate arrays, programmable array logic components, or any other device or devices that may be configured to process electronic signals.

It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer in a number of ways or all of the functionality may be integrated into a dedicated, standalone image capture device. All such permutations and combinations are intended to fall within the scope of the present disclosure.

It will also be appreciated that means for performing the steps associated with the processes described above may include any suitable components of the image capture system 100 described above with reference to FIG. 1, along with any software and/or hardware suitable for controlling operation of same. The user interfaces described herein may, for example, be rendered within the display 110 of the image capture system 100 of FIG. 1. All such realizations and means for performing the processes disclosed herein are intended to fall within the scope of this disclosure.

While the invention has been disclosed in connection with certain preferred embodiments, other embodiments will be recognized by those of ordinary skill in the art, and all such variations, modifications, and substitutions are intended to fall within the scope of this disclosure. Thus, the invention is to be understood with reference to the following claims, which are to be interpreted in the broadest sense allowable by law.

What is claimed is:

1. A method for operating a scanning system that includes a scanning device and a display, the scanning device adapted for continuous acquisition of surface data from a subject, the scanning device having one or more scanning parameters, and the display adapted for displaying a digital surface reconstruction containing a plurality of three-dimensional points recovered from the surface data, the method comprising:

rendering the digital surface reconstruction in the display; and providing a visual cue within the display that relates to the one or more scanning parameters;

wherein the one or more scanning parameters includes a range of distances for data capture, providing a visual cue further including color coding a plurality of rendered points of the digital surface reconstruction according to a current distance of each one of the plurality of rendered points relative to the range of distances for data capture;

wherein color coding includes rendering points more distant than the range of distances in a first color;

wherein color coding includes rendering points nearer than the range of distances in a second color;

wherein color coding includes rendering points within the range of distances in a third color.

2. The method of claim 1 wherein rendering the digital surface reconstruction includes rendering the digital surface reconstruction from a current point of view of the scanning device.

3. The method of claim 2 further comprising superimposing the digital surface reconstruction and a video image of the subject from the current point of view in the display.

4. The method of claim 1 wherein rendering the digital surface reconstruction includes rendering the digital surface reconstruction in real time.

5. The method of claim 1 wherein the one or more parameters includes an optimal distance from the scanning device to a subject.

6. The method of claim 1 wherein the one or more scanning parameters includes a field of view for data capture within the display, the visual cue including a box bounding the field of view.

7. The method of claim 6 wherein the one or more scanning parameters includes a range of distances for data capture within the display, the visual cue including a three-dimensional box bounding the field of view and the range of distances.

8. The method of claim 1 wherein the visual cue includes a dynamic object within the display, the dynamic object adapted to convey information relating to a distance between the scanning device and a subject of the surface data.

9. The method of claim 8 wherein the dynamic object includes an animated bullseye.

10. The method of claim 8 wherein the dynamic object relates to a most recent frame of surface data.

11. The method of claim 8 wherein the dynamic object provides a relative distance indicator for visual feedback to a user concerning whether the scanning device is at least one of too close, too far, or properly distanced from the subject.

12. The method of claim 11 wherein the relative distance indicator provides graduated feedback to assist a user in maintaining a proper scan distance.

13. The method of claim 1 wherein the distance between the scanning device and the subject is calculated as a mean distance from a plurality of points within a field of view of the scanning device.

14. The method of claim 1 further comprising capturing a two-dimensional video image with the scanning device and rendering the video image on the display.

15. The method of claim 14 further comprising superimposing the digital surface reconstruction on the video image in the display.

16. The method of claim 14 wherein the visual cue is updated at a video rate of the two-dimensional video image.

17. The method of claim 1 wherein the visual cue is updated in real time.

* * * * *